(12) United States Patent
Müller et al.

(10) Patent No.: US 7,368,414 B2
(45) Date of Patent: May 6, 2008

(54) FUNGICIDAL MIXTURES

(75) Inventors: Bernd Müller, Frankenthal (DE); Arne Ptock, Ludwigshafen (DE); Eberhard Ammermann, Heppenheim (DE); Reinhard Stierl, Mutterstadt (DE); Gisela Lorenz, Hambach (DE); Siegfried Strathmann, Limburgerhof (DE); Maria Scherer, Landau (DE); Klaus Schelberger, Gönnheim (DE); Joachim Leyendecker, Hassloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 663 days.

(21) Appl. No.: 10/450,130

(22) PCT Filed: Dec. 13, 2001

(86) PCT No.: PCT/EP01/14635

§ 371 (c)(1),
(2), (4) Date: Jun. 11, 2003

(87) PCT Pub. No.: WO02/49438

PCT Pub. Date: Jun. 27, 2002

(65) Prior Publication Data

US 2004/0116492 A1    Jun. 17, 2004

(30) Foreign Application Priority Data

Dec. 18, 2000    (DE) ................. 100 63 046

(51) Int. Cl.
  *A01N 47/40*    (2006.01)
  *A01N 47/28*    (2006.01)
(52) U.S. Cl. ........................ 504/141; 504/148
(58) Field of Classification Search ........... 424/405; 504/141, 148
  See application file for complete search history.

(56) References Cited

U.S. PATENT DOCUMENTS

| 5,824,705 A | 10/1998 | Mueller et al. |
| 5,869,517 A | 2/1999 | Mueller et al. |
| 6,020,354 A | 2/2000 | Assmann et al. |
| 6,169,056 B1 | 1/2001 | Bayer et al. |
| 6,207,692 B1 | 3/2001 | Mueller et al. |
| 6,297,236 B1 | 10/2001 | Stenzel et al. |
| 6,316,480 B1 | 11/2001 | Schelberger |
| 6,365,614 B1 | 4/2002 | Schelberger |
| 6,559,136 B1 * | 5/2003 | Mauler-Machnik et al. .. 514/63 |

FOREIGN PATENT DOCUMENTS

| CA | 2215514 | 10/1996 |
| CA | 2289638 | 12/1998 |
| EP | 298 196 | 1/1989 |
| WO | 93/15046 | 8/1993 |
| WO | 90/01256 | 1/1996 |
| WO | 96/01258 | 1/1996 |
| WO | 96/32015 | 10/1996 |
| WO | 97/06171 | 2/1997 |
| WO | 97/10716 | 3/1997 |
| WO | 98/47370 | 10/1998 |
| WO | 98/48628 | 11/1998 |
| WO | 98/53689 | 12/1998 |
| WO | 98/53690 | 12/1998 |
| WO | 98/58544 | 12/1998 |

OTHER PUBLICATIONS

The e-Pesticide Manual (11th Ed.), Version 1.1, XP-002200538.
Pesticide Biochemistry and Physiology 71, 107-115, Mitani et al., 107-115.

* cited by examiner

Primary Examiner—Alton Pryor
(74) Attorney, Agent, or Firm—Novak Druce + Quigg LLP

(57) ABSTRACT

Fungicidal mixtures, comprising
A) carbamates of the formula I,

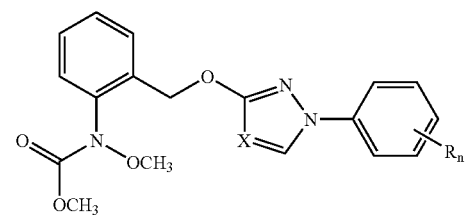

I in which X is CH or N, n is 0, 1 or 2 and R is halogen, $C_1$-$C_4$-alkyl or $C_1$-$C_4$-haloalkyl, where the radicals R can be different if n is 2, one of its salts or adducts and,
B) imidazole derivatives of the formula II

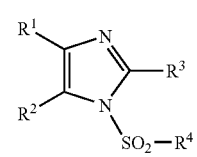

II in which $R^1$ and $R^2$ are halogen or phenyl, which may be substituted by halogen or alkyl, or
  $R^1$ and $R^2$ together with the bridging C=C double bond form a 3,4-difluoromethylenedioxyphenyl group;
$R^3$ is cyano or halogen, and
$R^4$ is dialkylamino or
  isoxazol-4-yl, which may carry two alkyl radicals,
in a synergistically effective amount, methods for controlling harmful fungi using mixtures of the compounds I and II and the use of the compounds I and II for preparing such mixtures are described.

11 Claims, No Drawings

FUNGICIDAL MIXTURES

The present invention relates to fungicidal mixtures, comprising
A) carbamates of the formula I,

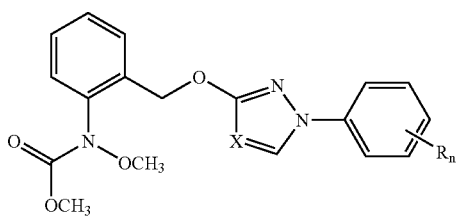

I in which X is CH or N, n is 0, 1 or 2 and R is halogen, $C_1$-$C_4$-alkyl or $C_1$-$C_4$-haloalkyl, where the radicals R can be different if n is 2, one of its salts or adducts and,
B) imidazole derivatives of the formula II

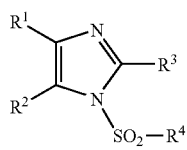

II in which $R^1$ and $R^2$ are halogen or phenyl, which may be substituted by halogen or $C_1$-$C_4$-alkyl, or
$R^1$ and $R^2$ together with the bridging C=C double bond form a 3,4-difluoromethylenedioxyphenyl group;
$R^3$ is cyano or halogen, and
$R^4$ is di($C_1$-$C_4$-alkyl)amino or isoxazol-4-yl, which may carry two $C_1$-$C_4$-alkyl radicals, in a synergistically effective amount.

Moreover, the invention relates to methods for controlling harmful fungi using mixtures of the compounds I and II, and to the use of the compounds I and the compounds II for preparing such mixtures.

The compounds of the formula I, their preparation and their action against harmful fungi are known from the literature (WO-A 93/15046; WO-A 96/01256 and WO-A 96/01258).

The imidazole derivatives of the formula II, their preparation and their action against harmful fungi are likewise known (EP-A 298 196, WO-A 97/06171).

It is an object of the present invention to provide mixtures which, at a reduced total amount of active compounds applied, have an improved action against harmful fungi (synergistic mixtures), with a view to reducing the application rates and improving the activity spectrum of the known compounds I and II.

We have found that this object is achieved by the mixture defined at the outset. Furthermore we have found that, if the compounds I and the compounds II are applied simultaneously, whether jointly or separately, or if the compounds I and the compounds II are applied successively, harmful fungi can be controlled better than with the individual compounds on their own.

The formula I represents in particular carbamates in which the combination of the substituents corresponds to one row of the table below:

I

| No.  | X  | $R_n$ |
|------|----|-------|
| I-1  | N  | 2-F |
| I-2  | N  | 3-F |
| I-3  | N  | 4-F |
| I-4  | N  | 2-Cl |
| I-5  | N  | 3-Cl |
| I-6  | N  | 4-Cl |
| I-7  | N  | 2-Br |
| I-8  | N  | 3-Br |
| I-9  | N  | 4-Br |
| I-10 | N  | 2-$CH_3$ |
| I-11 | N  | 3-$CH_3$ |
| I-12 | N  | 4-$CH_3$ |
| I-13 | N  | 2-$CH_2CH_3$ |
| I-14 | N  | 3-$CH_2CH_3$ |
| I-15 | N  | 4-$CH_2CH_3$ |
| I-16 | N  | 2-$CH(CH_3)_2$ |
| I-17 | N  | 3-$CH(CH_3)_2$ |
| I-18 | N  | 4-$CH(CH_3)_2$ |
| I-19 | N  | 2-$CF_3$ |
| I-20 | N  | 3-$CF_3$ |
| I-21 | N  | 4-$CF_3$ |
| I-22 | N  | 2,4-$F_2$ |
| I-23 | N  | 2,4-$Cl_2$ |
| I-24 | N  | 3,4-$Cl_2$ |
| I-25 | N  | 2-Cl, 4-$CH_3$ |
| I-26 | N  | 3-Cl, 4-$CH_3$ |
| I-27 | CH | 2-F |
| I-28 | CH | 3-F |
| I-29 | CH | 4-F |
| I-30 | CH | 2-Cl |
| I-31 | CH | 3-Cl |
| I-32 | CH | 4-Cl |
| I-33 | CH | 2-Br |
| I-34 | CH | 3-Br |
| I-35 | CH | 4-Br |
| I-36 | CH | 2-$CH_3$ |
| I-37 | CH | 3-$CH_3$ |
| I-38 | CH | 4-$CH_3$ |
| I-39 | CH | 2-$CH_2CH_3$ |
| I-40 | CH | 3-$CH_2CH_3$ |
| I-41 | CH | 4-$CH_2CH_3$ |
| I-42 | CH | 2-$CH(CH_3)_2$ |
| I-43 | CH | 3-$CH(CH_3)_2$ |
| I-44 | CH | 4-$CH(CH_3)_2$ |
| I-45 | CH | 2-$CF_3$ |
| I-46 | CH | 3-$CF_3$ |
| I-47 | CH | 4-$CF_3$ |
| I-48 | CH | 2,4-$F_2$ |
| I-49 | CH | 2,4-$Cl_2$ |
| I-50 | CH | 3,4-$Cl_2$ |
| I-51 | CH | 2-Cl, 4-$CH_3$ |
| I-52 | CH | 3-Cl, 4-$CH_3$ |

Particular preference is given to the compounds I-12, I-23, I-32 and I-38.

Preference is given to compounds of the formula II in which $R^1$ is halogen, in particular chlorine, and $R^2$ is tolyl, in particular p-tolyl.

Preference is also given to compounds of the formula II in which $R^4$ is dimethylamino.

In addition, particular preference is given to the compound of the formula IIa (common name: cyazofamid). This compound is known from EP-A 298 196.

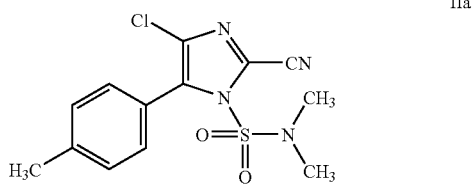

IIa

Preference is furthermore given to compounds of the formula II in which $R^1$ and $R^2$ together with the bridging C=C double bond form a 3,4-difluoromethylenedioxyphenyl group.

In addition, preference is given to compounds of the formula II in which $R^4$ is 3,5-dimethylisoxazol-4-yl.

Particular preference is given to the compounds of the formula IIb in which X is halogen.

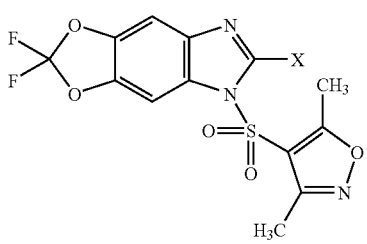

IIb

Halogen denotes fluorine, chlorine, bromine and iodine. Particular preference is given to compounds of the formula IIb in which X is bromine (IIb.1) or chlorine (IIb.2).

Owing to the basic character of their nitrogen atoms, the compounds I and II are capable of forming salts or adducts with inorganic or organic acids or with metal ions.

Examples of inorganic acids are hydrohalic acids, such as hydrogen fluoride, hydrogen chloride, hydrogen bromide and hydrogen iodide, sulfuric acid, phosphoric acid and nitric acid.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of from 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals of from 1 to 20 carbon atoms), arylphosphonic acids or aryldiphosphonic acids (aromatic radicals, such as phenyl and naphthyl, which carry one or two phosphonic acid radicals), it being possible for the alkyl or aryl radicals to carry further substituents, for example p-toluenesulfonic acid, salicylic acid, p-aminosalicylic acid, 2-phenoxybenzoic acid, 2-acetoxybenzoic acid, etc.

Suitable metal ions are, in particular, the ions of the elements of the first to eighth transition group, in particular chromium, manganese, iron, cobalt, nickel, copper, zinc, and additionally those of the second main group, in particular calcium and magnesium, and of the third and fourth main group, in particular aluminum, tin and lead. If appropriate, the metals can exist in the various valencies which they can assume.

When preparing the mixtures, it is preferred to employ the pure active compounds I and II, to which further active compounds against harmful fungi or other pests, such as insects, arachnids or nematodes, or else herbicidal or growth-regulating active compounds or fertilizers can be admixed.

The mixtures of the compounds I and II, or the compounds I and II, applied simultaneously, i.e. jointly or separately, exhibit outstanding activity against a wide range of phytopathogenic fungi, in particular from the classes of the Ascomycetes, Basidiomycetes, Phycomycetes and Deuteromycetes. Some of them act systemically and can therefore be employed also as foliar- and soil-acting fungicides.

They are especially important for controlling a large number of fungi in a variety of crop plants, such as cotton, vegetable species (for example cucumbers, beans, tomatoes, potatoes and cucurbits), barley, grass, oats, bananas, coffee, maize, fruit species, rice, rye, soya, grapevine, wheat, ornamentals, sugarcane, and a variety of seeds.

They are particularly suitable for controlling the following phytopathogenic fungi: *Blumeria graminis* (powdery mildew) in cereals, *Erysiphe cichoracearum* and *Sphaerotheca fuliginea* in cucurbits, *Podosphaera leucotricha* in apples, *Uncinula necator* in grapes *Puccinia* species in cereals, *Rhizoctonia* species in cotton, rice and lawns, *Ustilago* species in cereals and sugarcane, *Venturia inaequalis* (scab) in apples, *Helminthosporium* species in cereals, *Septoria nodorum* in wheat, *Botrytis cinerea* (gray mold) in strawberries, vegetables, ornamentals and grapes, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapes, *Pseudoperonaspora* species in hops and cucumbers, Alternaria species in vegetables and fruit, *Mycosphaerella* species in bananans and also *Fusarium* and *Verticillium* species.

Furthermore, they can be used in the protection of materials (for example in the protection of wood), for example against *Paecilomyces variotii*.

The compounds I and II can be applied simultaneously, either together or separately, or in succession, the sequence, in the case of separate application, generally not having any effect on the result of the control measures.

The compounds I and II are usually used in a weight ratio of from 20:1 to 1:100, in particular from 5:1 to 1:100, preferably from 2:1 to 1:80.

Depending on the kind of effect desired, the application rates of the mixtures according to the invention are, in particular in the case of areas under agricultural cultivation, from 0.01 to 8 kg/ha, preferably from 0.1 to 5 kg/ha, in particular from 0.1 to 3.0 kg/ha.

The application rates of the compounds I are generally from 0.01 to 2.5 kg/ha, more specifically from 0.01 to 1 kg/ha, preferably from 0.05 to 0.5 kg/ha, in particular from 0.05 to 0.3 kg/ha.

The application rates of the compounds II are correspondingly generally from 0.01 to 10 kg/ha, more specifically from 0.01 to 1 kg/ha, preferably from 0.02 to 0.5 kg/ha, in particular from 0.05 to 0.3 kg/ha.

For seed treatment, the application rates of the mixture are generally from 0.001 to 250 g/kg of seed, preferably from 0.01 to 100 g/kg, in particular from 0.01 to 50 g/kg.

If phytopathogenic fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated, for example, in the form of directly sprayable solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a manner known per se, for example by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, for example ligno-, phenol-, naphthalene- and dibutylnaphthalene-sulfonic acid, and of fatty acids, alkyl- and alkylaryl-sulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methyl cellulose.

Powders, materials for broadcasting and dusts can be prepared by mixing or jointly grinding the compounds I and II, or the mixture of the compounds I and II with a solid carrier.

Granules (for example coated granules, impregnated granules or homogeneous granules) are usually prepared by binding the active compound, or active compounds, to a solid carrier.

Fillers or solid carriers are, for example, mineral earths, such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably from 0.5 to 90% by weight, of one of the compounds I and II or of the mixture of the compounds I and II. The active compounds are employed in a purity of from 90% to 100%, preferably from 95% to 100% (according to NMR spectrum or HPLC).

The compounds I and II, or the mixtures, or the corresponding formulations, are applied by treating the harmful fungi, their habitat or the plants, seeds, soils, areas, materials or spaces to be kept free from them with a fungicidally effective amount of the mixture, or of the compounds I and II in the case of separate application.

Application can be effected before or after infection by the harmful fungi.

USE EXAMPLE

The synergistic activity of the mixtures according to the invention was demonstrated by the following experiments:

The active compounds, separately or together, were formulated as 10% emulsion in a mixture of 63% by weight of cyclohexanone and 27% by weight of emulsifier, and diluted with water to the desired concentration.

Evaluation was carried out by determining the infected leaf areas in percent. These percentages were converted into efficacies. The efficacy (w) was calculated as follows using Abbot's formula:

$$w = (1-\alpha) \cdot 100/\beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active compounds were determined using Colby's formula [R. S. Colby, Weeds 15, 20-22 (1967)] and compared with the observed efficacies.

$$\text{Colby Formula: } E = x + y - x \cdot y/100$$

E expected efficacy, expressed in % of the untreated control, when using the mixture of the active compounds A and B at the concentrations a and b x efficacy, expressed in % of the untreated control, when using the active compound A at a concentration a y efficacy, expressed in % of the untreated control, when using the active compound B at a concentration b

USE EXAMPLE

Activity Against Downy Mildew of Grapes Caused by *Plasmopara viticola*

Leaves of potted vines of the cultivar "Müller-Thurgau" were sprayed to run off point with an aqueous preparation of active compound which had been prepared from a stock solution comprising 10% of active compound, 85% of cyclohexanone and 5% of emulsifier. The next day, the undersides of the leaves were inoculated with an aqueous zoospore suspension of *Plasmopara viticola*. The vines were then initially placed at 24° C. in a chamber saturated with water vapor for 48 hours and then for 5 days in a greenhouse at 20-30° C. After this period of time, the plants were once more placed into a moist chamber for 16 hours to promote sporangiophore eruption. The extent of the development of the disease on the undersides of the leaves was then determined visually.

TABLE A

Individual active compounds

| Example | Active compound | Concentration of active compound in the spray liquor [ppm] | Efficacy in % of the untreated control |
|---|---|---|---|
| 1 | Control (untreated) | (70% infection) | 0 |
| 2 | I-23 | 0.25 | 29 |
|  |  | 0.06 | 0 |
| 3 | I-32 | 0.25 | 71 |
|  |  | 0.06 | 29 |
| 4 | I-38 | 0.25 | 50 |
|  |  | 0.06 | 14 |
| 5 | IIa | 4 | 71 |
|  |  | 1 | 57 |
|  |  | 0.25 | 14 |
| 6 | IIb.1 | 4 | 57 |
|  |  | 1 | 29 |
|  |  | 0.25 | 14 |

TABLE B

Combinations according to the invention

| Example | Mixture of active compounds concentration mixing ratio | Observed efficacy | Calculated efficacy*) |
|---|---|---|---|
| 7 | I-23 + IIa<br>0.25 + 4 ppm<br>1:16 | 93 | 80 |
| 8 | I-23 + IIa<br>0.06 + 1 ppm<br>1:16 | 64 | 41 |
| 9 | I-23 + IIa<br>0.06 + 4 ppm<br>1:64 | 86 | 71 |
| 10 | I-23 + IIa<br>0.25 + 0.25 ppm<br>1:1 | 57 | 39 |
| 11 | I-23 + IIa<br>0.06 + 0.25 ppm<br>1:4 | 43 | 14 |
| 12 | I-32 + IIa<br>0.06 + 1 ppm<br>1:16 | 71 | 45 |
| 13 | I-32 + IIa<br>0.06 + 4 ppm<br>1:64 | 93 | 80 |
| 14 | I-32 + IIa<br>0.25 + 0.25 ppm<br>1:1 | 86 | 76 |
| 15 | I-32 + IIa<br>0.06 + 0.25 ppm<br>1:4 | 64 | 39 |
| 16 | I-38 + IIa<br>0.06 + 1 ppm<br>1:16 | 57 | 43 |
| 17 | I-38 + IIa<br>0.06 + 4 ppm<br>1:64 | 86 | 76 |
| 18 | I-38 + IIa<br>0.25 + 0.25 ppm<br>1:1 | 79 | 57 |
| 19 | I-38 + IIa<br>0.25 + 1 ppm<br>1:4 | 93 | 79 |
| 20 | I-38 + IIa<br>0.06 + 0.25 ppm<br>1:4 | 57 | 27 |
| 21 | I-23 + IIb.1<br>0.25 + 4 ppm<br>1:16 | 86 | 69 |
| 22 | I-23 + IIb.1<br>0.06 + 1 ppm<br>1:16 | 43 | 20 |
| 23 | I-23 + IIb.1<br>0.06 + 4 ppm<br>1:64 | 71 | 57 |
| 24 | I-23 + IIb.1<br>0.25 + 0.25 ppm<br>1:1 | 50 | 39 |
| 25 | I-23 + IIb.1<br>0.25 + 1 ppm<br>1:4 | 64 | 49 |
| 26 | I-23 + IIb.1<br>0.06 + 0.25 ppm<br>1:4 | 29 | 14 |
| 27 | I-32 + IIb.1<br>0.25 + 4 ppm<br>1:16 | 99 | 88 |
| 28 | I-32 + IIb.1<br>0.06 + 1 ppm<br>1:16 | 57 | 37 |
| 29 | I-32 + IIb.1<br>0.06 + 4 ppm<br>1:64 | 79 | 69 |
| 30 | I-32 + IIb.1<br>0.25 + 0.25 ppm<br>1:1 | 86 | 76 |
| 31 | I-32 + IIb.1<br>0.06 + 0.25 ppm<br>1:4 | 64 | 39 |
| 32 | I-38 + IIb.1<br>0.25 + 4 ppm<br>1:16 | 93 | 79 |
| 33 | I-38 + IIb.1<br>0.06 + 1 ppm<br>1:16 | 50 | 29 |
| 34 | I-38 + IIb.1<br>0.06 + 4 ppm<br>1:64 | 79 | 63 |
| 35 | I-38 + IIb.1<br>0.25 + 0.25 ppm<br>1:1 | 71 | 57 |
| 36 | I-38 + IIb.1<br>0.25 + 1 ppm<br>1:4 | 86 | 64 |
| 37 | I-38 + IIb.1<br>0.06 + 0.25 ppm<br>1:4 | 57 | 27 |

*) calculated using Colby's formula

The test results show that, for all mixing ratios, the observed efficacy is higher than that calculated beforehand using Colby's formula.

We claim:
1. A fungicidal mixture, comprising
A) carbamates of the formula I,

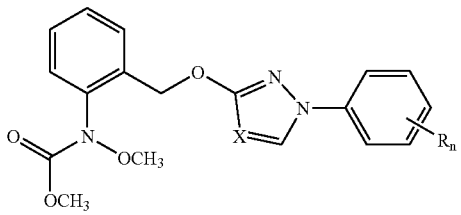

in which X is CH or N, n is 0, 1 or 2 and R is halogen, $C_1$-$C_4$-alkyl or $C_1$-$C_4$-haloalkyl, where the radicals R can be different if n is 2, one of its salts or adducts and,
B) imidazole derivatives of the formula II

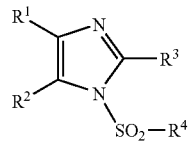

in which
 $R^1$ and $R^2$ are halogen or phenyl, which may be substituted by halogen or $C_1$-$C_4$-alkyl, or
 $R^1$ and $R^2$ together with the bridging C=C double bond form a 3,4-difluoromethylenedioxyphenyl group;
 $R^3$ is cyano or halogen, and
 $R^4$ is di($C_1$-$C_4$-alkyl) amino or
  isoxazol-4-yl, which may carry two $C_1$-$C_4$-alkyl radicals,
in a synergistically effective amount.

2. A fungicidal mixture as claimed in claim 1, wherein the imidazole derivative II corresponds to the formula IIa

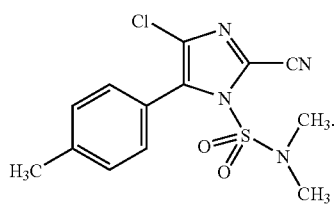

3. A fungicidal mixture as claimed in claim 1, wherein the imidazole derivative II corresponds to the formula IIb

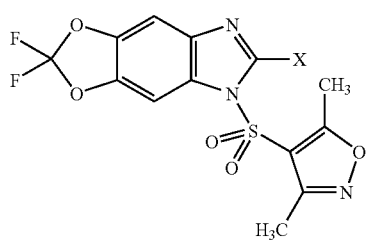

where X is chlorine or bromine.

4. A fungicidal mixture as claimed in claims 1, wherein the weight ratio of the carbamates I to the imidazole derivatives of the formula II is from 20:1 to 1:100.

5. A method for preparing a fungicidally active synergistic mixture as claimed in claim 1, which comprises combining the carbamates of the formula I and the imidazole derivatives of the formula II in synergistically effective amounts.

6. A method as claimed in claim 5, which further comprises adding solvents and/or carriers to the carbamates of the formula I.

7. A method as claimed in claim 5, which further comprises adding solvents and/or carriers to the imidazole derivatives of the formula II.

8. A method for controlling harmful fungi, which comprises treating the harmful fungi, their habitat or plants, seeds, soils, areas, materials or spaces to be kept free from them with synergistically effective amounts of
A) carbamates of the formula I

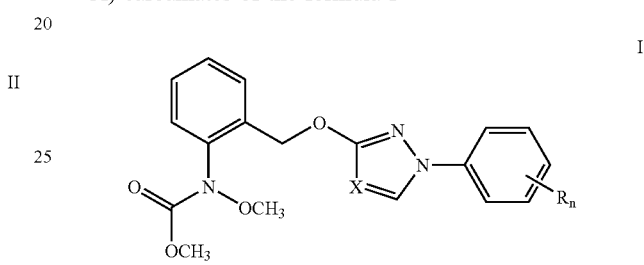

in which X is GB or N, n is 0, 1 or 2 and R is halogen, $C_1$-$C_4$-alkyl or $C_1$-$C_4$-haloalkyl, where the radicals R can be different if n is 2, one of its salts or adducts, and
B) imidazole derivatives of the formula II

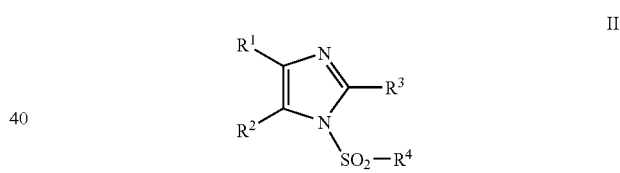

in which
 $R^1$ and $R^2$ are halogen or phenyl, which may be substituted by halogen or $C_1$-$C_4$-alkyl, or
 $R^1$ and $R_2$ together with the bridging C=C double bond form a 3,4-difluoromethylenedioxyphenyl group;
 $R^3$ is cyano or halogen, and
 $R^4$ is di($C_1$-$C_4$-alkyl)amino or isoxazol-4-yl, which may carry two $C_1$-$C_4$-alkyl radicals, such as to form a synergistic mixture of (A) and (B).

9. A method as claimed in claim 8, wherein the carbamates of the formula I and the imidazole derivatives of the formula II are applied simultaneously, i.e. either jointly or separately, or successively.

10. A method as claimed in claim 8, wherein the carbamates of the formula I are applied in an amount of from 0.01 to 2.5 kg/ha.

11. A method as claimed in claim 8, wherein the imidazole derivatives of the formula II are applied in an amount of from 0.01 to 10 kg/ha.

* * * * *

UNITED STATES PATENT AND TRADEMARK OFFICE
CERTIFICATE OF CORRECTION

PATENT NO.          : 7,368,414 B2
APPLICATION NO.  : 10/450130
DATED                   : May 6, 2008
INVENTOR(S)         : Müller et al.

It is certified that error appears in the above-identified patent and that said Letters Patent is hereby corrected as shown below:

On the Title of the Patent:

Item (30) Foreign Application Priority Data:
"Dec. 18, 2000" should read --Dec. 13, 2000--

In Claim 1, col. 9, indicated line 18:
"its salts or adducts and" should read
--its salts or adducts with inorganic or organic acids or with metal ions and--

In Claim 4, col. 10, indicated line 1:
"in claims 1" should read --in claim 1--

In Claim 8, col. 10, indicated line 31:
"X is GB or N" should read --X is CH or N--

In Claim 8, col. 10, indicated line 33:
"its salts or adducts, and" should read
--its salts or adducts with inorganic or organic acids or with metal ions, and--

In Claim 8, col. 10, indicated line 48:
"$R^1$ and $R_2$ together" should read --$R^1$ and $R^2$ together--

Signed and Sealed this

Twenty-third Day of March, 2010

David J. Kappos
*Director of the United States Patent and Trademark Office*